United States Patent [19]

Nohara et al.

[11] Patent Number: 4,672,073
[45] Date of Patent: Jun. 9, 1987

[54] DIPHENOXYPROPANE DERIVATIVES, ITS PRODUCTION AND USE 5-TETRAZOLYL SUBSTITUTED DIPHENOXYPROPANES AND MEDICAL COMPOSITIONS THEREOF

[75] Inventors: Akira Nohara; Yoshitaka Maki, both of Kyoto, Japan

[73] Assignee: Takeda Chemical Industries, Ltd., Osaka, Japan

[21] Appl. No.: 795,103

[22] Filed: Nov. 5, 1985

Related U.S. Application Data

[62] Division of Ser. No. 440,297, Nov. 9, 1982, Pat. No. 4,567,201.

[30] Foreign Application Priority Data

Oct. 22, 1982 [JP] Japan ................................ 57-186361
Nov. 25, 1982 [JP] Japan ................................ 57-189812

[51] Int. Cl.⁴ .................... C07D 257/04; A61K 31/41
[52] U.S. Cl. ..................................... 514/381; 548/253
[58] Field of Search ......................... 548/253; 514/381

[56] References Cited

U.S. PATENT DOCUMENTS

3,600,437  8/1971  Marshall .............................. 548/252

FOREIGN PATENT DOCUMENTS

0080371 10/1982 European Pat. Off. .
2058785  4/1981 United Kingdom .

OTHER PUBLICATIONS

Nodine et al, "Animal and Clinical Pharm. Techniques in Drug Evaluation", pp. 492–500, Year Book Med. Pub. Inc. Chicago, Ill. (1964).

Primary Examiner—Glennon H. Hollrah
Assistant Examiner—D. B. Springer
Attorney, Agent, or Firm—Wegner & Bretschneider

[57] ABSTRACT

A diphenoxypropane derivative of the formula:

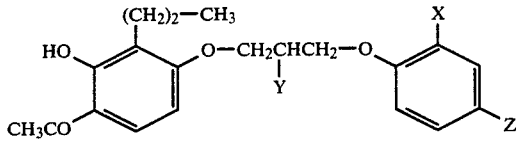

wherein X is a halogen atom, Y is a hydrogen atom or a hydroxy group and Z is a tetrazolyl or carboxy group, has excellent antiasthmatic and antiinflammatory activities, and therefore the diphenoxypropane derivatives are useful as antiasthmatic or antiiflammatory agents.

7 Claims, No Drawings

DIPHENOXYPROPANE DERIVATIVES, ITS PRODUCTION AND USE 5-TETRAZOLYL SUBSTITUTED DIPHENOXYPROPANES AND MEDICAL COMPOSITIONS THEREOF

This application is a divisional of Ser. No. 440,297, filed Nov. 9, 1982, now U.S. Pat. No. 4,567,201, issued 1/28/86.

This invention relates to diphenoxypropane derivatives, a method of producing the same and their use.

A synthetic research for compounds which would antagonize chemical mediators exerting contractile effects on bronchial smooth muscle led to the discovery that certain diphenoxypropane derivatives is useful for the purpose. The diphenoxypropane derivatives according to this invention are subsumed in the general formula given in U.K. Patent Application Publication No. 2,058,785, but have not been specifically described in the working examples thereof. Under the circumstances the present inventors undertook a further pharmacological study of these diphenoxypropane derivatives and found that these diphenoxypropane derivatives have excellent activity. This finding was followed by further studies, on which this invention has been predicated.

Thus, the present invention relates to (1) a diphenoxypropane derivative (I) of the formula:

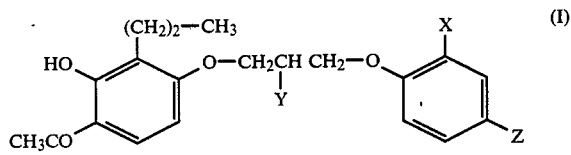

wherein X is a halogen atom, Y is a hydrogen atom or a hydroxy group, Z is a tetrazolyl or carboxy group; (2) a method of producing a diphenoxypropane derivative (I), which comprises reacting a compound (II) of the formula:

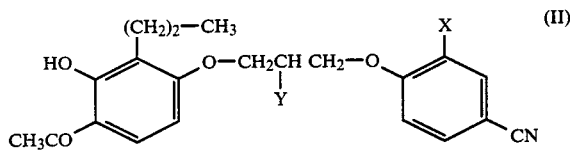

wherein X and Y have the same meaning as defined above, with hydrazoic acid or a salt thereof or subjecting a compound (III) of the formula:

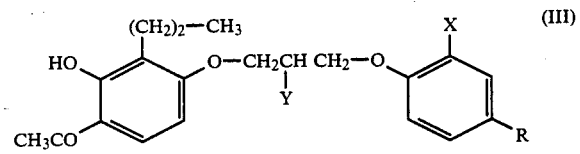

wherein X and Y are as defined above and R is a cyano, carbamoyl or alkoxycarbonyl group, to hydrolysis, and (3) an antiasthmatic or antiinflammatory agent which contains the diphenoxypropane derivative (I).

Referring to the above general formula, the halogen atom X may for example be chlorine, bromine, iodine or fluorine. Among them, chlorine and bromine are preferable.

In the present specification, the compound (I) wherein Z is a tetrazolyl group is sometimes referred to as "compound (I)-A", and the compound (I) wherein Z is a carboxy group is sometimes referred to as "compound (I)-B".

The compound (I)-A according to this invention is produced by the following procedure. Thus, it is produced by reacting a compound (II) with hydrazoic acid or a salt thereof. The salt of hydrazoic acid as used in this reaction is exemplified by salts of hydrazoic acid with alkali metals (e.g. lithium azide, sodium azide, potassium azide, etc.), salts of hydrazoic acid with alkaline earth metals (e.g. magnesium azide, calcium azide, barium azide, strontium azide), salts of N₃H with other metals which are capable of forming salts therewith (e.g. aluminum azide, tin azide, titanium azide), salts of hydrazoic acid with ammonia or organic bases such as aniline, etc. While these salts of hydrazoic acid may be used independently, it is possible to use an alkali metal salt of hydrazoic acid, e.g. sodium azide, in combination with a Lewis acid (e.g. aluminum chloride, stannic chloride, zinc chloride, titanium tetrachloride) or ammonium chloride. It is likely that in such a combination, the alkali metal azide forms a hydrazoate with the cation of the compound used in combination, e.g. aluminum azide, tin azide, zinc azide, titanium azide, ammonium azide or the like, and this hydrazoate reacts with the starting compound (II). Among hydrazoic acid, salts thereof and combinations of salts, the combination of sodium azide with ammonium chloride is particularly desirable.

Generally, the reaction is desirably conducted in an organic solvent. Examples of such solvent include hydrocarbons such as benzene, toluene, petroleum ether, etc., ethers such as tetrahydrofuran, dioxane, ethylene glycol dimethyl ether, etc., acetonitrile, dimethylformamide, formamide, dimethyl sulfoxide, etc. The temperature, time and other conditions of the reaction are not particularly critical, but the reaction is generally conducted at about 50° to 150° C. for about 1 hour to 2 days.

When a salt of hydrazoic acid is used as another reactant in this reaction, the compound (I)-A is produced in the form of a salt corresponding to the salt of hydrazoic acid used due to the acidity of the tetrazole ring and this salt can be easily converted to the desired compound (I)-A having a free tetrazole ring by treating it with a suitable acid (such as a mineral acid, e.g. hydrochloric acid, sulfuric acid, etc.).

Moreover, an organic amine salt, amino acid salt, alkali metal salt or ammonium salt, for instance, of the compound (I)-A can be produced by reacting (I)-A with an organic amine such as ethanolamine, dl-methylephedrine, 1-(3,5-dihydroxyphenyl)-L-isopropylaminoethanol, isoproterenol, dextromethorphan, hetrazan (diethylcarbamazine), etc., an amino acid such as L-lysine, an alkali metal hydroxide such as sodium hydroxide, potassium hydroxide, etc., or ammonia in the per se conventional manner, e.g. mixing and heating in a suitable solvent.

The starting compound (II) of this invention wherein Y is a hydroxy group can be produced by reacting a compound of the formula:

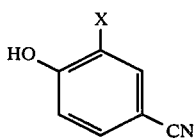 (IV)

wherein X is defined as above, with a compound of the formula:

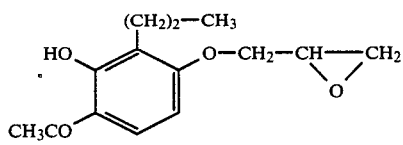 (V)

or by reacting a compound of the formula:

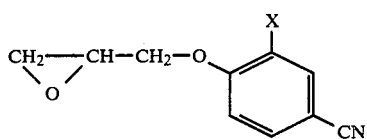 (VI)

wherein X is defined as above, with a compound of the formula:

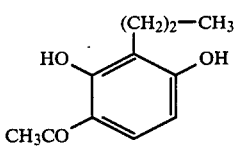 (VII)

The starting compound (II) of this invention wherein Y is a hydrogen atom can be produced by reacting a compound of general formula (IV) with a compound of the formula:

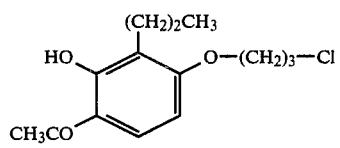 (VIII)

or by reacting a compound (VII) with a compound of the formula:

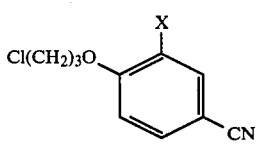 (IX)

wherein X is defined as above.

The reaction is preferably conducted in the presence of a base. The base is exemplified by ammonium hydroxide (e.g. benzyltrimethylammonium hydroxide, benzyltriethylammonium hydroxide), organic amines (e.g. triethylamine, tributylamine), and alkali carbonate (e.g. anhydrous potassium carbonate, potassium hydrogen carbonate, sodium hydrogen carbonate).

Generally, the reaction is desirably conducted in an organic solvent. As examples of such organic solvents may be mentioned dimethylformamide, formamide, dimethyl sulfoxide, hexamethylphosphoric triamide, various ethers (e.g. tetrahydrofuran, dioxane), alkyl halides (e.g. chloroform, dichloromethane), etc. While the reaction temperature, time and other conditions are not especially critical, the reaction is generally conducted at room temperature to about 180° C. for about 1 to 24 hours.

The compound (I)-B can be produced by the following method. Thus, compound (I)-B is produced by subjecting the compound (III) to hydrolysis with an acid or alkali. The acid to be used in hydrolysis includes, among others, sulfuric acid, hydrochloric acid or other inorganic acids, and the alkali includes such hydroxides as sodium hydroxide, potassium hydroxide, lithium hydroxide or barium hydroxide. Generally, the reaction is preferably carried out in an organic solvent. The solvent includes, among others, alcohols such as methanol, ethanol or propanol, organic acids such as acetic acid or formic acid, and ethers such as tetrahydrofuran or dioxane. The reaction temperature, reaction time and other reaction conditions are not critical, but in general the reaction is carried out at a temperature between about 50° C. and about the boiling point of the solvent used for about 1 to 48 hours.

Moreover, an organic amine salt, amino acid salt, alkali metal salt or ammonium salt, for instance, of the compound (I)-B can be produced by reacting the compound (I)-B with an organic amine such as ethanolamine, dl-methylephedrine, 1-(3,5-dihydroxyphenyl)-L-isopropylaminoethanol, isoproterenol, dextromethorphan, hetrazan (diethylcarbamazine), etc., and amino acid such as L-lysine, an alkali metal hydroxide such as sodium hydroxide, potassium hydroxide, etc., or ammonia in the per se conventional manner, e.g. mixing and heating in a suitable solvent.

The starting compound (III) in which Y is a hydroxy group, can be prepared, for example, by reacting a compound of the formula:

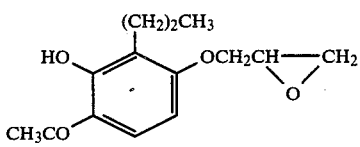 (X)

with a compound of the formula:

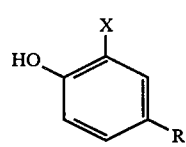 (XI)

wherein X and R are as defined above, or by reacting a compound of the formula:

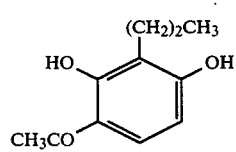 (XII)

with a compound of the formula:

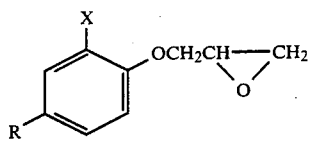

(XIII)

wherein X and R are as defined above. The compound (III) in which Y is a hydrogen atom can be prepared, for example, by reacting the compound of formula (XII) with a compound of the formula:

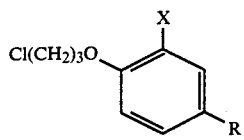

(XIV)

wherein X and R are as defined above.

The reaction is preferably conducted in the presence of a base. The base is exemplified by ammonium hydroxide (e.g. benzyltrimethylammonium hydroxide, benzyltriethylammonium hydroxide), organic amines (e.g. triethylamine, tributylamine), and alkali carbonate (e.g. anhydrous potassium carbonate, potassium hydrogen carbonate, sodium hydrogen carbonate).

Generally, the reaction is desirably conducted in an organic solvent. As examples of such organic solvents may be mentioned dimethylformamide, formamide, dimethyl sulfoxide, hexamethylphosphoric triamide, various ethers (e.g. tetrahydrofuran, dioxane), alkyl halides (e.g. chloroform, dichloromethane), etc. While the reaction temperature, time and other conditions are not especially critical, the reaction is generally conducted at room temperature to about 180° C. for about 1 to 24 hours.

In cases where R is a cyano group, said compounds may be converted either to the compound (I)-b by directly subjecting to hydrolysis or to the compound (III) in which R is an ester group by reacting with an alcohol such as methanol or ethanol in the presence of an acid such as sulfuric acid or hydrochloric acid.

The compound (I) according to this invention exhibits an antagonistic action on the slow reacting substance of anaphylaxis (SRS-A) which is a chemical mediator known to induce a contraction of bronchial and other smooth muscles.

Furthermore, compound (I) displays antiinflammatory activity as well.

SRS-A is produced by various stimuli such as immune reactions and has been considered to be an important mediator of bronchospasm in immediate allergies such as allergic asthma. There are several types of SRS-A, such as leukotriene C(LTC), leukotriene D(LTD), etc., and it is known that LTD and LTC are substantially equivalent in activity on the human bronchial muscle and that LTD is superior to LTC in constrictive effect on the guniea pig ileum [S. E. Dahlen et al., Nature 288, 484 (1980); R. A. Lewis et al., Biochemical and Biophysical Research Communications 96, 271 (1980)]. The antagonistic effect of drugs against SRS-A can be investigated using the guinea pig ileum [R. A. Appleton et al., Journal of Medicinal Chemistry 20, 371 (1977)] and since SRS-A is a mixture of LTC, LTD, etc., it is desirable to use a synthetic SRS-A in the investigation of antagonistic activity.

The present inventors studied the antagonistic action of compound (I)-A against SRS-A using a synthetic $LTD_4$ in the following manner.

(1) Test Method

The inhibitory effect of the drug on the contractile response (60-70% of maximum contraction) of the ileum of guinea pig (body weight 300-350 g, female and male) to leukotriene $D_4$ ($LTD_4$) was investigated. In Tyrode solution containing atropine ($10^{-7}M$) and mepyramine ($10^{-6}M$), $3 \times 10^{-10}$ or $10^{-9}M$ of $LTD_4$ was repeatedly permitted to act on the guinea pig ileum and after the amplitude of contraction had become constant, a solution of the test drug was added to a final concentration of $10^{-9}$ to $10^{-4}M$. After 1 minute, the same concentration of $LTD_4$ was further added and the anti-SRS-A activity of the drug was calculated from the change in contraction amplitude by means of the following equation.

Percent inhibition =

$$\frac{\text{Amplitude of } LTD_4 - \text{Amplitude of } LTD_4 -}{\text{Amplitude of } LTD_4 - \text{induced contraction}} \times 100$$
$$\text{induced construction} \quad \text{induced construction}$$
$$\text{before addition of drug} \quad \text{after addition of drug}$$
$$\text{before addition of drug}$$

To obtain the $IC_{50}$ value, the mole concentration of the drug showing a 50% inhibition of the contractile response was determined from plots on a graph.

The drug was used as dissolved in dimethyl sulfoxide. The solvent was used in an amount less than 1% which would not exert any influence on the ileum.

(2) Results

The concentrations of compounds necessary to cause a 50% inhibition of the $LTD_4$-induced contraction (60 to 70% of maximum contraction) of the guinea pig ileum are shown in $IC_{50}(M)$ values below.

TABLE 1

| Anti-SRS-A activity | |
| --- | --- |
| Drug | $IC_{50}$ (M) |
| Compound (I)-A-1 | $4.1 \times 10^{-9}$ |
| Compound (I)-A-2 | $1.9 \times 10^{-8}$ |
| Compound (I)-A-3 | $7.0 \times 10^{-8}$ |
| Control compound-1 | $4.2 \times 10^{-7}$ |
| Control compound-2 | $6.8 \times 10^{-7}$ |

(Note)
Compound (I)-A-1: Compound (I)-A wherein X=Cl and Y=OH
Compound (I)-A-2: Compound (I)-A wherein X=Br and Y=OH
Compound (I)-A-3: Compound (I)-A wherein X=Cl and Y=H
Control compound-1: Compound which has the formula:

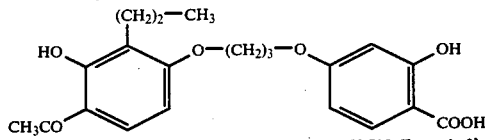

[See U.K. Patent Application Publication No. 2,058,785, Example 8].
Control compound-2: Compound of the formula:

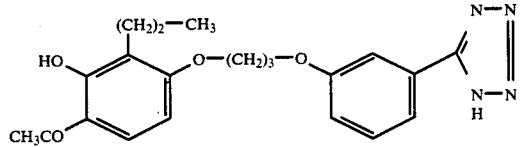

[See U.K. Patent Application Publication No. 2,058,785, Example 10 (b)]

The above test results indicate that the compound (I)-A according to this invention is superior to the compounds shown in the examples of U.K. Patent Application Publication No. 2,058,785.

Furthermore, against the bronchoconstriction in guinea pigs due to an intravenous administration of synthetic leukotriene D4 (LTD4), compound (I)-A-1 as intravenously administered 2 minutes before LTD4 dosing displayed a remarkable inhibitory effect.

(1) Test method

Guinea pigs of Hartley strain, both male and female, with body weights about 400 g were assigned to groups of 6 individuals, and the bronchoconstriction due to LTD4 were measured according to the method of Konzett-Rössler, [Konzett, H. and Rössler, R.: Naunyn-Schmiedebergs Archiv für Experimentelle Pathologie und Pharmakologie 195, 71–74 (1940)]. Each guinea pig was fixed in supine position under urethane anesthesia (1.5 g/kg, intraperitoneal) and the trachea was incised and connected to an artificial respiration apparatus, Rodent Respirator Model 680 [Harvard Apparatus Company, U.S.A.] via a cannula. The branch tube of this tracheal cannula was connected to Bronchospasm Transducer Model 7020 [Ugobasil Biological Research Apparatus, Italy]. Under the conditions of 5 to 7 ml of air per stroke, 70 strokes per minute and a lung loading pressure of 10 cmH2O, the volume of overflowing air was recorded on Rectigraph-8S (Sanei Sokki Ltd., Japan) via a transducer. After administration of gallamine triethiodide (1 mg/kg, i.v.), 10 μg/kg of histamine.2HCl was intravenously administered to investigate the response of the animal. Then, a solution of LTD4 in physiological saline (10 μg/kg) was intravenously administered and the bronchoconstriction elicited thereby was recorded for 15 minutes. Two minutes before LTD4 loading, compound (I)-A-1 was intravenously administered in a volume of 0.1 ml per 100 g body weight. Compound (I)-A-1 and LTD4 were administered through a cannula inserted into the jugular vein.

The compound (I)-A-1 was used as dissolved in physiological saline containing sodium hydrogen carbonate, and LTD4 was taken from a stock stored in methanol (1 mg/1 ml methanol) at −70° C.

(2) Result

Effect of compound (I)-A-1 against bronchoconstriction due to LTD4:

The bronchoconstriction induced by intravenous administration of 10 μg/kg of LTD4 as given 2 minutes after the administration of physiological saline was maximal at the time of 30 seconds after the administration of LTD4 and, since then, was rapidly attenuated to about 50% at the time of 2 minutes but lasted till 15 minutes. Assuming that the response at complete obstruction is 100%, the values at 30 seconds and 15 minutes were 47.4±6.9% (n=6, Mean ± S.E.) and 19.4±2.8% (Mean ± S.E.), respectively (S.E.: standard error).

The administration of Compound (I)-A-1 at the dose levels of 0.08, 0.313, 1.25 and 5 mg/kg at the time of 2 minutes before LTD4 dosing inhibited the above response by 39, 41, 51 and 93%, respectively, relative to the maximum response. Thus, at the intravenous dose of 5 mg/kg, a substantially complete inhibition could be accomplished (See Table 2, below). These results support the in vitro anti-SRS-A activity data.

TABLE 2

| Compound | Dosage (mg/kg, i.v.) | Number of animals | Percent increase of overflow | Percent inhibition |
|---|---|---|---|---|
| Physiological saline | — | 6 | 47.4 ± 6.9 | — |
| Compound (I)-A-1 | 0.08 | 8 | 29.1 ± 7.5 | 39 |
| Compound (I)-A-1 | 0.313 | 6 | 28.1 ± 7.1 | 41 |
| Compound (I)-A-1 | 1.25 | 6 | 23.4 ± 8.0* | 51 |
| Compound (I)-A-1 | 5 | 6 | 3.3 ± 2.1*** | 93 |

Note:
Significant difference in relation to physiological saline control:
*$p < 0.05$,
***$p < 0.001$,
i.v. = intravenous administration Furthermore, as will be apparent from the test result given below, the compound (I)-A-1 has an antiinflammatory activity.

Carrageenin edema in rats:

The volume of the right hind paw of each rat was measured and the test compound suspended in 4% gum arabic solution was orally administered in an amount of 1 ml/100 g body weight. Immediately thereafter, a further amount of water was given to make the total dosing volume 5 ml. After 1 hour, 0.05 ml of a 1% suspension of caragéenin in physiological saline was subcutaneously injected into the foot pad. Three hours after the carrageenin injection, the volume of the paw was measured again and the volume of the edema was calculated as a difference between this measured volume of the paw and the volume before the injection.

In the case of intravenous administration, a solution of the test compound in an aqueous solution of NaHCO3 was intravenously administered in an amount of 2.0 ml/100 g body weight and 5 ml of water per animal was orally administered. Then, carrageenin was injected subcutaneously to produce edema.

TABLE 3

| Test compound | Dosage (mg/kg) | Route of administration | Mean volume of edematous swelling ± S.E. | Percent inhibition |
|---|---|---|---|---|
| Control | — | p.o. | 0.573 ± 0.021 | — |
| Compound (I)-A-1 | 50 | p.o. | 0.487 ± 0.023* | 15.0 |
| Control | — | i.v. | 0.547 ± 0.034 | — |
| Compound (I)-A-1 | 1 | i.v. | 0.442 ± 0.044 | 19.2 |
| Compound (I)-A-1 | 10 | i.v. | 0.410 ± 0.046* | 25.0 |

Note
*$p < 0.05$
p.o.: oral
i.v.: intravenous
S.E.: standard error

The acute toxicity of compound (I)-A-1 in mice was found to be as follows.

(1) Method

Five 5-week-old male mice of Jcl:ICR strain, weighing 26.0 to 30.5 g, were used. Compound (I)-A-1 was suspended in a 5% solution of gum arabic and administered orally by gastric gavage at the level of 0.2 ml per 10 grams body weight.

(2) Results

The oral administration of compound (I)-A-1 in a dose of 500 mg/kg caused no symptoms that could be attributable to compound (I)-A-1. Autopsy after 1 week did not reveal any abnormalities.

Then the present inventors studied the antagonistic action of the compound (I)-B against SRS-A using a synthetic LTD4 in the manner described on the compound (I)-A.

(Note)
Compound (I)-B-1: Compound (I)-B wherein X=Cl and Y=OH
Compound (I)-B-2: Compound (I)-B wherein X=Cl and Y=H The results are shown in Table 4.

In each case, the bronchoconstriction following intravenous administration of 10 μg/kg of $LTD_4$ at 2 or 30 minutes after the administration of physiological saline reached a maximum 30 seconds after the administration of $LTD_4$, and then decreased to about 50% at 2 minutes after the administration of $LTD_4$. The response continued for 15 minutes after the administration of $LTD_4$. Repeated experiments using 6 animals per group gave mean degrees of maximum bronchoconstriction (30-second values) of 52.2–67.1% and 54.7–70.1%, respectively, as compared with the state of complete obstruction (100%). In experiment 1, the test compounds (I)-B-1, (I)-B-2 and Control compound-1 were each intravenously administered at two minutes before the administration of $LTD_4$ and inhibitory effect on the bronchoconstriction was examined. The minimum effective doses (causing statistically significant differences as compared with the control group; significance level >5%) were 0.313, 0.313 and 5 mg/kg, respectively. The corresponding inhibition percentages were 41, 52 and 56%, respectively. In experiment 2, the test compounds were intravenously administered 30 minutes before the administration of $LTD_4$ and the effect on the above response was examined. The minimum effective doses were 5, 5, and 20 mg/kg, respectively.

The above results thus proved that Compounds (I)-B-1 and (I)-B-2 are superior to Control compound-1 in the inhibitory effect upon the bronchoconstriction.

TABLE 4

| Compound | % Inhibition Dose (mg/kg, i.v.) | | | |
|---|---|---|---|---|
| | 0.313 | 1.25 | 5 | 20 |
| Experiment 1 | | | | |
| Compound (I)-B-1 | 41* | 51** | 84*** | NT |
| Compound (I)-B-2 | 52* | 77** | 79** | NT |
| Control compound-1 | NT | 14 | 56*** | 87*** |
| Experiment 2 | | | | |
| Compound (I)-B-1 | NT | NT | 42** | 96*** |
| Compound (I)-B-2 | NT | 10 | 42** | 66*** |
| Control compound-1 | NT | NT | 14 | 35** |

Notes:
Experiment 1: The test compounds were intravenously administered 2 minutes before the intravenous administration of 10 μg/kg of $LTD_4$.
Experiment 2: The test compounds were intravenously administered 30 minutes before the intravenous administration of 10 μg/kg of $LTD_4$.
% Inhibition: Each value was calculated from the volume (in percentage) of air overflowing from the respiratory tract at the time when the response was maximal, i.e. 30 seconds after the administration of $LTD_4$.
NT: Not tested.
*P < 0.05,
**P < 0.01,
***P < 0.001 (against the control group)

Further, studies were carried out on antigen-induced bronchoconstriction in sensitized guinea pigs using the compounds (I)-B-1, (I)-B-2 and the Control compound-1.

According to the method of Orange and Moore [Orange, R. P. and Moore, E. G., Journal of Immunology, 116, 392–397 (1976)], Hartley-strain male guinea pigs weighing about 350 g were sensitized by intraperitoneal administration of 1 ml of an emulsion composed of 0.5 ml of physiological saline containing 1 mg of egg alubumin (EA) and 0.5 ml of Freund's complete adjuvant (Difco, USA). Three weeks after the sensitization, the serum antibody levels in the sensitized guinea pigs were determined by the 3-hour PCA reaction in guinea pigs and those guinea pigs that gave positive results in the PCA reaction with 1,000-fold diluted serum samples therefrom were used as the sensitized aminals. Using the Konzett-Rössler method as mentioned under the above paragraph (i), the bronchoconstriction due to the antigen-antibody reaction was induced by intravenous administration of 1 mg/kg of the antigen EA instead of $LTD_4$, and recorded.

The results are shown in Table 5.

The bronchoconstriction in the control group as induced by antigen administration 2 minutes after the intravenous administration of physiological saline reached a maximum one minute after the intravenous administration of the antigen. Gradual recovery followed and the pretreatment state was almost restored in 15 minutes after the induction. Repeated experiments using 6 animals per group gave mean degrees of maximum bronchoconstriction (one-minute values) of 72.8–83.3% as compared with the state of complete obstruction (100%). The test compounds (I)-B-1, (I)-B-2 and Control compound-1 were each intravenously administered 2 minutes prior to antigen administration and the inhibitory effect on the bronchoconstriction was examined. The minimum effective doses were 5, 5 and 20 mg/kg, respectively, and the corresponding inhibition percentages were 51, 52 and 64%, respectively.

The above results indicated that Compounds (I)-B-1 and (I)-B-2 are superior to Control compound-1 in the inhibitory effect on the antigen-induced bronchoconstriction.

TABLE 5

| Compound | % Inhibition Dose (mg/kg, i.v.) | | |
|---|---|---|---|
| | 1.25 | 5 | 20 |
| Compound (I)-B-1 | 6 | 51*** | 75*** |
| Compound (I)-B-2 | 20 | 52** | 88*** |
| Control compound-1 | 12 | 16 | 64*** |

Notes:
The test compounds were intravenously administered 2 minutes prior to intravenous administration of the antigen.
% Inhibition: Each value was calculated from the volume (in percentage) of air overflowing from the respiratory tract at the time when the response was maximal, i.e. one minute after administration of the antigen.
**P < 0.01,
***P < 0.001 (against the control group).

The acute toxicity of compounds (I)-B-1 and (I)-B-2 in mice was found to be as follows.

(1) Method

Five 5-week-old male mice of Jcl:ICR strain, weighing 26.0 to 30.5 g, were used. Compound (I)-B-1 or (I)-B-2 was suspended in a 5% solution of gum arabic and administered orally by gastric gavage at the level of 0.2 ml per 10 grams body weight.

(2) Result

The oral administration of compound (I)-B-1 or (I)-B-2 in a dose of 500 mg/kg caused no symptoms that could be attributable to compound (I)-B-1 or (I)-B-2. Autopsy after 7 days did not reveal any abnormalities.

It will thus be apparent that the compound (I) according to this invention is useful in the treatment of diseases due to SRS-A, such as asthma, hay fever, chronic bronchitis, allergic diseases of the eye, allergic diseases of the stomach and intestines, cardiovascular disturbances, allergic dermatitis and other inflammatory diseases. For example, as an antiasthmatic or antiinflammatory drug, the compound (I) or said salt thereof can be administered orally or parenterally to mammalian animals (e.g. mouse, rat, guinea pig, man) in a daily dose of about 1 to 20 mg/kg.

For oral administration, the compound (I) or salt thereof can be formulated with a pharmaceutically acceptable carrier (e.g. lactose, starch, cellulose derivatives, stearic acid, magnesium stearate, sucrose, gelatin, gum arabic) and processed into such doses forms as tablets, capsules, granules, troches, liquid, syrup, etc. For parenteral administration, the compound (I) or salt thereof can be formulated with pharmacologically acceptable vehicles (e.g. vaseline, hydrophilic ointment bases, oleaginous bases, glyceride, polyethylene glycol, etc.) and processed into ointments, suppositories, aerosols, inhalants, injections, etc. These dosage forms may be produced by the established pharmaceutical procedures.

The following Reference Examples and Examples illustrate the present invention in more detail.

REFERENCE EXAMPLE 1

To a solution of 4-cyano-2-chlorophenol (612 mg), dimethylformamide (2 ml) and Triton B (Rohm and Haas, U.S.A.) (1 drop) was added 4-(2,3-epoxy)propyl-2-hydroxy-3-n-propylacetophenone (500 mg), and the mixture was heated at 170° C. for 0.5 hour. A further amount (500 mg) of 4-cyano-2-chlorophenol was added, and the mixture was further heated at 170° C. for one hour. After the solvent was distilled off, a small amount of ethanol was added to the oily residue and the mixture was cooled to crystallize. The crystals were collected by filtration and recrystallized from ethanol to give 760 mg of crystals of 4-[3-(2-chloro-4-cyanophenoxy)-2-hydroxypropoxy]-2-hydroxy-3-n-propylacetophenone. m.p. 143°–145° C.

Elemental analysis: $C_{21}H_{22}ClNO_5$: Calcd.: C, 62.45; H, 5.49; N, 3.47. Found: C, 62.38; H, 5.60; N, 3.29.

Nuclear magnetic resonance spectrum $(CDCl_3)\delta$: 12.65 (1H, s), 7.38–7.65 (3H, m), 6.97 (1H, dd, J=2 and 8 Hz), 6.43 (1H, d, J=9 Hz), 4.32 (5H, pseudo-s), ca. 2.6 (2H), 2.55 (3H, s), ca. 1.43 (2H, m), 0.90 (3H, t, J=7 Hz).

Infrared absorption spectrum $(KBr)cm^{-1}$: 3440, 2240, 1630, 1610.

REFERENCE EXAMPLE 2

A mixture of 4-(2,3-epoxy)propyl-2-hydroxy-3-propylacetophenone (1 g), 3-bromo-4-hydroxybenzonitrile (792 mg), dimethylformamide (2 ml) and Triton B (1 drop) was heated at 170° C. for one hour. The solvent was distilled off and after addition of water, the residue was extracted twice, with ethyl acetate, and the extract was washed with water and dried over sodium sulfate. The solvent was then distilled off and the residue was chromatographed on a column of silica gel (50 g) and eluted with a solution of chloroform-acetone-formic acid (100:1:0.1). This product was recrystallized from methanol to give 825 mg of 4-[3-(2-bromo-4-cyanophenoxy)-2-hydroxypropoxy]-2-hydroxy-3-propylacetophenone as colorless plates. m.p. 143°–145° C.

Elemental analysis: $C_{21}H_{22}BrNO_5$: Calcd.: C, 56.26; H, 4.95; N, 3.12. Found: C, 56.51; H, 4.96; N, 3.18.

Nuclear magnetic resonance spectrum $(CDCl_3)\delta$: 12.62 (1H, s), 7.72 (1H, d, J=2 Hz), 7.53 (1H, d, J=9 Hz), 7.52 (1H, dd, J=2 and 8 Hz), 6.93 (1H, d, J=8 Hz), 6.44 (1H, d, J=9 Hz), 4.30 (5H, m), 2.63 (2H, t, J=7 Hz), 2.54 (3H, s), 1.52 (2H, m), 0.89 (3H, t, J=7 Hz).

Infrared absorption spectrum $(KBr)cm^{-1}$: 3440, 2230, 1625, 1500.

REFERENCE EXAMPLE 3

A mixture of 3-(2-chloro-4-cyanophenoxy)propyl chloride (1.61 g), 2,4-dihydroxy-3-n-propylacetophenone (1.27 g), potassium carbonate (970 mg), potassium iodide (600 mg) and dimethylformamide (3 ml) was stirred under heating at 120° C. for 5 hours. The reaction mixture was diluted with 1N-HCl and extracted with ethyl acetate. The extract was washed with water and dried over sodium sulfate, and the solvent was distilled off. The residue was cooled and the crystals which formed were collected by filtration and recrystallized twice from methanol to give 1.40 g of 1-(4-acetyl-3-hydroxy-2-n-propylphenoxy)-3-(2-chloro-4-cyanophenoxy)propane as colorless crystals melting at 96°–97° C.

Infrared absorption spectrum $(KBr)cm^{-1}$: 2225, 1640–1610.

Nuclear magnetic resonance spectrum $(CDCl_3)\delta$: 12.69 (1H, s), 7.56 (1H, pseudo-s), 7.52 (1H, d, J=9 Hz), 7.48 (1H, dd, J=2 and 8 Hz), 6.93 (1H, d, J=8 Hz), 6.43 (1H, d, J=9 Hz), 4.28 (4H, t, J=5.5 Hz), 2.62 (2H, t, J=7 Hz), 2.58 (3H, s), 2.42 (2H), 1.42 (2H, m), 0.88 (3H, t, J=7 Hz).

Elemental analysis: $C_{21}H_{22}ClNO_4$: Calcd.: C, 65.03; H, 5.72; N, 3.61. Found: C, 65.34; H, 5.75; N, 3.72.

REFERENCE EXAMPLE 4

A mixture of 2-chloro-4-cyanophenol (2.15 g), 3-bromo-1-chloropropane (2.3 g), dimethylformamide (3 ml) and potassium carbonate (1.5 g) was heated at 100° C. for one hour. After the inorganic salt was filtered off, the solvent was distilled off and the residue was dissolved in chloroform. The solution was chromatographed on a column of silica gel (80 g) and eluted with a solution of petroleum ether-ethyl acetate (10:1) to give 3.06 g of 3-(2-chloro-4-cyanophenoxy)propyl chloride as a colorless oil.

Nuclear magnetic resonance spectrum $(CDCl_3)\delta$: 7.51 (1H, d, J=2 Hz), 7.60 (1H, dd, J=2 and 8 Hz), 6.97 (1H, d, J=8 Hz), 4.24 (2H, t, J=5.5 Hz), 3.79 (2H, t, J=6 Hz), 2.37 (2H, m).

REFERENCE EXAMPLE 5

While a solution of 2-chloro-4-cyanophenol (50 g) and epichlorohydrin (60.3 g) in ethanol (55 ml) was refluxed, a solution of potassium hydroxide (21.9 g) in ethanol (90 ml) was added dropwise over a period of 40 minutes and the reaction mixture was further refluxed for 100 minutes. After the mixture was cooled, water (50 ml) was added thereto and it was neutralized with 1N hydrochloric acid. After the solvent was distilled off, the residue was extracted with diethyl ether. The extract was dried (over magnesium sulfate) and the diethyl ether was distilled off. The residue was distilled under reduced pressure to give 27 g of 3-chloro-4-(2,3-epoxy)propylbenzonitrile as a colorless oil. After crystallization, the crystals are recrystallized from isopropyl ether-ethyl acetate to give colorless needles. m.p. 71.0°–71.8° C.

Elemental analysis: $C_{10}H_8ClNO_2$: Calcd.: C, 57.30; H, 3.85; N, 6.68. Found: C, 57.16; H, 3.88; N, 6.60.

REFERENCE EXAMPLE 6

A mixture of 2-chloro-4-cyanophenol (2.15 g), 3-bromo-1-chloropropane (2.3 g), dimethylformamide (3 ml) and potassium carbonate (1.5 g) was heated at 100° C. for one hour. The inorganic salt was then filtered off and the solvent was distilled off. The residue was dissolved in chloroform, chromatographed on a column of silica gel (80 g), and eluted with a solution of petroleum ether-ethyl acetate (10:1) to give 3-(2-chloro-4-cyanophenoxy)propyl chloride as a colorless oil (3.06 g).

REFERENCE EXAMPLE 7

A mixture of 1-(4-acetyl-3-hydroxy-2-n-propylphenoxy)-3-(2-chloro-4-cyanophenoxy)propane (1.86 g), ethanol (30 ml) and concentrated sulfuric acid (10 ml) was refluxed for 6 hours and then cooled to room temperature. The crystals were collected by filtration and dissolved in chloroform, the solution was washed with a saturated aqeuous sodium hydrogen carbonate solution and then with dilute hydrochloric acid and dried (sodium sulfate). Then, the chloroform was distilled off, and the residue was recrystallized from ethanol. There was obtained ethyl 4-[3-(4-acetyl-3-hydroxy-2-n-propylphenoxy)propoxy]-3-chlorobenzoate as colorless needles (1.1 g). Melting point 101°–102° C.

REFERENCE EXAMPLE 8

A mixture of 2-bromo-4-cyanophenol (3.96 g), 3-bromopropyl chloride (3.46 g), dimethylformamide (20 ml) and anhydrous potassium carbonate (3 g) was heated at 100° C. for 0.5 hour. The inorganic salt was filtered off, and the filtrate was concentrated. The residue was chromatographed on a column of silica gel (90 g), and eluted with a solution of n-hexane-chloroform-acetone (20:10:1) to give 3-(2-bromo-4-cyanophenoxy)propyl chloride as a colorless oil (4.15 g).

REFERENCE EXAMPLE 9

A mixture of 2,4-dihydroxy-3-n-propylacetophenone (2.83 g), 3-(2-bromo-4-cyanophenoxy)propyl chloride (4.0 g), anhydrous potassium carbonate (2.00 g), potassium iodide (200 mg) and dimethylformamide (10 ml) was heated at 120° C. for 2 hours. The reaction mixture was then diluted with water, and extracted three times with ethyl acetate. The extract was washed with water and dried over sodium sulfate, the ethyl acetate was distilled off, and the residue was recrystallized from methanol to give 1-(4-acetyl-3-hydroxy-2-n-propylphenoxy)-3-(2-bromo-4-cyanophenoxy)propane as pale brown needles (3.96 g). Melting point 88°–89° C.

REFERENCE EXAMPLE 10

A mixture of 1-(4-acetyl-3-hydroxy-2-n-propylphenoxy)-3-(2-bromo-4-cyanophenoxy)propane (2.5 g), ethanol (35 ml) and concentrated sulfuric acid (10 ml) was refluxed for 6 hours and then allowed to stand at room temperature. The crystals were collected by filtration and dissolved in chloroform, and the solution was washed with aqueous sodium hydrogen carbonate and then with 1N hydrochloric acid and dried over sodium sulfate. The solvent was distilled off and the residue was recrystallized from ethanol to give ethyl 4-[3-[(4-acetyl-3-hydroxy-2-n-propyl)phenoxy]propoxy]-3-bromobenzoate as colorless needles (1.70 g). Melting point 99°–100° C.

REFERENCE EXAMPLE 11

A mixture of 2-bromo-4-cyanophenol (1.584 g), 4-(2,3-epoxypropyl)-2-hydroxy-3-n-propylacetophenone (2.0 g), dimethylformamide (3 ml) and Triton B (one drop) was heated at 160°–170° C. for one hour. The reaction mixture was diluted with water and extracted with ethyl acetate. The extract was dried over sodium sulfate, the solvent was distilled off, and the residue was crystallized by adding methanol. Crystals of 4-[3-(2-bromo-4-cyanophenoxy)-2-hydroxypropoxy]-2-hydroxy-3-n-propylacetophenone (1.8 g) were obtained. Melting point 141°–142° C.

REFERENCE EXAMPLE 12

A mixture of 2,4-dihydroxy-3-n-propylacetophenone (1.38 g), 3-chloro-4-(2,3-epoxypropyl)benzonitrile (1.5 g), dimethylformamide (3 ml) and Triton B (one drop) was heated at 160°–170° C. for 4 hours, then diluted with water and extracted with ethyl acetate. The extract was dried over sodium sulfate, the solvent was distilled off, and the residue was crystallized from ethanol to give 4-[3-(2-chloro-4-cyanophenoxy)-2-hydroxypropoxy]-2-hydroxy-3-n-propylacetophenone as crystals (1.3 g). Melting point 143°–145° C.

EXAMPLE 1

A mixture of 4-[3-(2-chloro-4-cyanophenoxy)-2-hydroxypropoxy]-2-hydroxy-3-propylacetophenone (760 mg), ammonium chloride (760 mg), sodium azide (760 mg) and dimethylformamide (2.5 ml) was heated at 120° C. for 1 hour. After the inorganic salt was filtered off, the dimethylformamide was distilled off. 1N-HCl was added to the residue and the mixture was extracted with ethyl acetate. The extract was washed with water and dried over sodium sulfate, and the solvent was distilled off. The residue was chromatographed on a column of silica gel (25 g) and eluted with a solution of chloroform-acetone-formic acid (5:1:0.1). The factions containing the desired product were combined and the solvent distilled off. To the residue was added a further amount of ethanol and chloroform and the mixture was re-distilled to obtain 640 mg of 4-[3-[4-(tetrazol-5-yl)-2-chlorophenoxy]-2-hydroxypropoxy]-2-hydroxy-3-propylacetophenone as a colorless amorphous solid.

Infrared absorption spectrum (KBr)cm$^{-1}$: 3400, 1630, 1500, 1270, 1120, 1065.

Nuclear magnetic resonance spectrum (DMSO-d$_6$)δ: 13.03 (1H, s), 8.18 (1H, pseudo-s), 8.10 (1H, dd, J=2 and 9 Hz), 7.90 (1H, d, J=9 Hz), 7.50 (1H, d, J=9 Hz), 6.77 (1H, d, J=9 Hz), 4.33 (5H, pseudo-s), 2.60 (3H, s), 1.47 (2H, m), 0.83 (3H, t, J=7 Hz).

Elemental analysis: $C_{21}H_{23}ClN_4O_5$: Calcd.: C, 56.44; H, 5.19; N, 12.54. Found: C, 56.02; H, 5.08; N, 12.66.

EXAMPLE 2

A mixture of 4-[3-(2-bromo-4-cyanophenoxy)-2-hydroxypropoxy]-2-hydroxy-3-propylacetophenone (695 mg), ammonium chloride (600 mg), sodium azide (300 mg) and dimethylformamide (3 ml) was heated at 120° C. for 1.5 hours, after which the inorganic salt was filtered off. The filtrate was concentrated and dilute hydrochloric acid was added to the concentrate. The mixture was extracted twice with ethyl acetate and the extract was washed with water and dried. The solvent was then distilled off and the residue was chromatographed on a column of silica gel (15 g), and eluted with a solution of chloroform-acetone-formic acid (5:1:0.1).

The eluate was concentrated, petroleum ether was added to the residue, and the mixture was concentrated to dryness. The procedure gave 620 mg of 2-hydroxy-3-propyl-4-[2-hydroxy-3-[2-bromo-4-(tetrazol-5-yl)phenoxy]propoxy]acetophenone as a colorelss amorphous solid.

Infrared absorption spectrum (KBr)cm$^{-1}$: 3370, 1620, 1270, 1120, 1055, 1020.

Nuclear magnetic resonance spectrum (DMSO-d$_6$)δ: 12.72 (1H, s), 8.18 (1H, d, J=2 Hz), 7.99 (1H, dd, J=2 and 8 Hz), 7.73 (1H, d, J=9 Hz), 7.33 (1H, d, J=8 Hz), 6.63 (1H, d, J=9 Hz), 4.26 (5H, s), 2.55 (3H, s), ca. 1.41 (2H, m), 0.81 (3H, t, J=7 Hz).

Elemental analysis: C$_{21}$H$_{23}$BrN$_4$O$_5$: Calcd.: C, 51.33; H, 4.72; N, 11.40. Found: C, 50.98; H, 4.59; N, 11.50.

EXAMPLE 3

A mixture of 1-(4-acetyl-3-hydroxy-2-n-propylphenoxy)-3-(2-chloro-4-cyanophenoxy)propane (776 mg), ammonium chloride (700 mg), sodium azide (700 mg) and dimethylformamide (2 ml) was heated at 120° C. for 1 hour. After the inorganic salt was filtered off, the filtrate was concentrated under reduced pressure. The residue was acidified with 1N-HCl and the resultant precipitate was recovered by filtration. Recrystallized from methanol gave 659 mg of 1-(4-acetyl-3-hydroxy-2-n-propylphenoxy)-3-[2-chloro-4-(tetrazol-5-yl)phenoxy]propane as white microcrystals. m.p. 214°–216° C.

Infrared absorption spectrum (KBr)cm$^{-1}$: 3100, 1620.

Nuclear magnetic resonance spectrum (DMSO-d$_6$)δ: 12.84 (1H, s), 8.09 (1H, pseudo-s), 8.02 (1H, dd, J=2 and 8 Hz), 7.80 (1H, d, J=9 Hz), 7.41 (1H, d, J=8 Hz), 6.68 (1H, d, J=9 Hz), 4.36 (4H, m), 2.57 (3H, s), ca. 2.4 (4H, m), 1.47 (2H, m), 0.83 (3H, t, J=7 Hz).

Elemental analysis: C$_{21}$H$_{23}$ClN$_4$O$_4$: Calcd.: C, 58.54; H, 5.38; N, 13.00. Found: C, 58.48; H, 5.31; N, 13.28.

EXAMPLE 4

A mixture of 4-[3-(2-chloro-4-cyanophenoxy)-2-hydroxypropoxy]-2-hydroxy-3-n-propylacetophenone (180 mg), ethanol (3 ml) and concentrated sulfuric acid (0.6 ml) was heated at 100° C. for 5 hours. The ethanol was then distilled off, the residue was diluted with water and extracted twice with ethyl acetate. The extract was washed with water and dried over sodium sulfate, the solvent was distilled off, and the residue was chromatographed on a column of silica gel (15 g) and eluted with a solution of chloroform-acetone-formic acid (20:1:0.1) to give an ester. Ethanol (2 ml) and a saturated aqueous sodium hydrogen carbonate solution (1 ml) were added to the ester, and the mixture was refluxed for 16 hours. The solvent was distilled off, the residue was acidified with 1N hydrochloric acid, and the mixture was extracted twice with ethyl acetate. The extract was washed with water and dried over sodium sulfate, the solvent was distilled off, and the residue was chromatographed on a column of silica gel (15 g), and eluted with a solution of chloroform-acetone-formic acid (7:1:0.1). The solvent was distilled off from the eluate, petroleum ether was added to the residue, and the white solid was collected by filtration and recrystallized from acetonitrile to give 4-[3-(4-acetyl-3-hydroxy-2-n-propylphenoxy)-2-hydroxypropoxy]-3-chlorobenzoic acid as colorless needles (58 mg). Melting point 100°–103° C.

EXAMPLE 5

A mixture of ethyl 4-[3-(4-acetyl-3-hydroxy-2-n-propylphenoxy)propoxy]-3-chlorobenzoate (1.0 g), ethanol (10 ml) and 1N sodium hydroxide (10 ml) was refluxed for 0.5 hour, then concentrated, acidified with 1N hydrochloric acid, and extracted with ethyl acetate. The extract was washed with water, dried over sodium sulfate and concentrated, and the crystals were collected by filtration. There was obtained 4-[3-(4-acetyl-3-hydroxy-2-n-propylphenoxy)propoxy]-3-chlorobenzoic acid as needles (840 mg). Melting point 171°–172° C.

EXAMPLE 6

A mixture of ethyl 4-[3-(4-acetyl-3-hydroxy-2-n-propylphenoxy)propoxy]-3-bromobenzoate (1.50 g), ethanol (15 ml) and 1N sodium hydroxide (10 ml) was refluxed for 0.5 hour, then concentrated, acidified with concentrated hydrochloric acid, and extracted with ethyl acetate. The extract was washed with water and dried over sodium sulfate, the solvent was distilled off, and the residue was chromatographed on a column of silica gel (50 g), and eluted with a solution of chloroform-acetone-formic acid (9:1:0.1). Recrystallization from ethyl acetate gave 4-[3-(4-acetyl-3-hydroxy-2-n-propylphenoxy)propoxy]-3-bromobenzoic acid as colorless needles (1.06 g). Melting point 180°–182° C.

EXAMPLE 7

A mixture of 4-[3-(2-bromo-4-cyanophenoxy)-2-hydroxypropoxy]-2-hydroxy-3-n-propylacetophenone (1.4 g), ethanol (12 ml) and concentrated sulfuric acid (4 ml) was refluxed for 4 hours, and then concentrated. Ethyl acetate and an aqueous sodium hydrogen carbonate solution were added. The ethyl acetate layer was separated and dried over sodium sulfate. The solvent was distilled off, and the residue was chromatographed on a column of silica gel, and eluated with dichloromethane. To thus obtained oil (1.5 g) were added ethanol (20 ml), water (50 ml) and 1N sodium hydroxide (6 ml). The mixture was refluxed for one hour and then concentrated. The residue was dissolved in water, treated with decoloring carbon and acidified with dilute hydrochloric acid, and the precipitate was collected by filtration and recrystallized from acetonitrile. There were obtained crystals (0.7 g) of 4-[3-(4-acetyl-3-hydroxy-2-n-propylphenoxy)-2-hydroxypropoxy]-3-bromobenzoic acid. Melting point 93°–94° C.

EXAMPLE 8

A mixture of 1-(4-acetyl-3-hydroxy-2-n-propylphenoxy)-3-(2-chloro-4-cyanophenoxy)propane (1 g), potassium hydroxide (2 g), water (5 ml) and ethanol (10 ml) was refluxed for 4 hours, then concentrated, acidified with dilute hydrochloric acid and extracted with ethyl acetate. The extract was dried over sodium sulfate, the solvent was distilled off and the residue was recrystallized from ethyl acetate to give 4-[3-(4-acetyl-3-hydroxy-2-n-propylphenoxy)propoxy]-3-chlorobenzoic acid as crystals (780 mg). Melting point 171°–172° C.

EXAMPLE 9

| Tablets | |
|---|---|
| (1) Compound (I)-A-1 | 20 mg |
| (2) Lactose | 150 mg |

| Tablets | |
|---|---|
| (3) Corn starch | 35 mg |
| (4) Microcrystalline cellulose | 30 mg |
| (5) Magnesium stearate | 5 mg |
| | 240 mg/tablet |

The above components are admixed and tableted by the established pharmaceutical procedure.

EXAMPLE 10

| Capsules | |
|---|---|
| (1) Compound (I)-A-1 | 20 mg |
| (2) Lactose | 102 mg |
| (3) Microcrystalline cellulose | 70 mg |
| (4) Magnesium stearate | 8 mg |
| | 200 mg/capsule |

The above components are encapsulated by the established pharmaceutical procedure.

EXAMPLE 11

| Tablets | |
|---|---|
| (1) Compound (I)-B-1 | 20 mg |
| (2) Lactose | 150 mg |
| (3) Corn starch | 35 mg |
| (4) Microcrystalline cellulose | 30 mg |
| (5) Magnesium stearate | 5 mg |
| | 240 mg/tablet |

The above components are admixed and tableted by the established pharmaceutical procedure.

EXAMPLE 12

| Capsules | |
|---|---|
| (1) Compound (I)-B-1 | 20 mg |
| (2) Lactose | 102 mg |
| (3) Microcrystalline cellulose | 70 mg |
| (4) Magnesium stearate | 8 mg |
| | 200 mg/capsule |

The above components are encapsulated by the established pharmaceutical procedure.

What we claim is:

1. A compound of the formula:

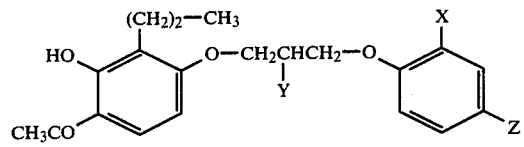

wherein X is chlorine or bromine, Y is a hydrogen atom or a hydroxy group and Z is a tetrazolyl group.

2. A compound as claimed in claim 1, wherein X is chlorine, Y is hydroxy and Z is tetrazolyl.

3. A compound as claimed in claim 1, wherein X is chlorine, Y is hydrogen and Z is tetrazolyl.

4. A compound as claimed in claim 1, wherein X is bromine, Y is hydroxy and Z is tetrazolyl.

5. A member of the class consisting of antiasthmatic and antiinflammatory agents which contains an effective antiasthmatic amount in the case of the antiasthmatic agents and an effective antiinflammatory amount in the case of the antiinflammatory agents of a compound of the formula

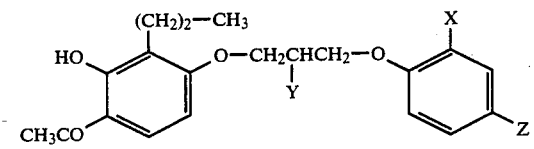

wherein X is chlorine or bromine, Y is a hydrogen atom or a hydroxy group and Z is a tetrazolyl group and a pharmaceutically acceptable carrier or vehicle therefore.

6. An antiasthmatic agent according to claim 5 containing an effective antiasthmatic amount of the said compound.

7. An antiinflammatory agent according to claim 5 containing an effective antiinflammatory amount of the said compound.